(12) United States Patent
Tajima

(10) Patent No.: US 6,867,419 B2
(45) Date of Patent: Mar. 15, 2005

(54) LASER DRIVEN COMPACT ION ACCELERATOR

(75) Inventor: Toshiki Tajima, Alamo, CA (US)

(73) Assignee: The Regents of the University of California, Oakland, CA (US)

(*) Notice: Subject to any disclaimer, the term of this patent is extended or adjusted under 35 U.S.C. 154(b) by 161 days.

(21) Appl. No.: 10/112,451

(22) Filed: Mar. 29, 2002

(65) Prior Publication Data

US 2003/0183774 A1 Oct. 2, 2003

(51) Int. Cl.⁷ .............................................. B01D 59/44
(52) U.S. Cl. .............................. 250/423 P; 250/423 R; 250/505.1
(58) Field of Search .................. 250/423 P, 423 R, 250/505.1, 424, 423, 396 R; 315/111.26; 356/316

(56) References Cited

U.S. PATENT DOCUMENTS

| | | | |
|---|---|---|---|
| 4,069,457 A | | 1/1978 | Martin et al. |
| 4,471,224 A | | 9/1984 | Cuomo et al. |
| 4,715,038 A | | 12/1987 | Fraser et al. |
| 4,734,579 A | * | 3/1988 | Lucatorto et al. ........... 250/282 |
| 4,937,532 A | | 6/1990 | Dawson et al. |
| 5,175,664 A | * | 12/1992 | Diels et al. ................. 361/213 |
| RE34,575 E | | 4/1994 | Klinkowstein et al. |
| 5,335,258 A | | 8/1994 | Whitlock |
| 5,373,156 A | * | 12/1994 | Franzen ...................... 250/288 |
| 5,382,914 A | | 1/1995 | Hamm et al. |
| 5,394,411 A | | 2/1995 | Milchberg et al. |
| 5,412,283 A | | 5/1995 | Trone |
| 5,440,133 A | | 8/1995 | Moyers et al. |
| 5,789,876 A | | 8/1998 | Umstadter et al. |
| 5,930,331 A | | 7/1999 | Rentzepis et al. |
| 6,061,379 A | * | 5/2000 | Schoen ........................ 372/76 |
| 6,534,764 B1 | * | 3/2003 | Verentchikov et al. ...... 250/287 |
| 2001/0032929 A1 | * | 10/2001 | Fuhrer et al. ............... 250/281 |
| 2002/0172317 A1 | * | 11/2002 | Maksimchuk et al. ...... 376/190 |
| 2002/0181655 A1 | * | 12/2002 | Schoen ........................ 378/119 |

FOREIGN PATENT DOCUMENTS

| | | |
|---|---|---|
| DE | 3616879 A | 11/1986 |
| JP | 06068984 A | 3/1994 |
| JP | 07169597 | 7/1995 |

OTHER PUBLICATIONS

Zhidkov, A., et al., "Energetic–multiple–charged–ion sources on short–laser–pulse irradiated foils," Review of Scientific Instruments, vol. 71, No. 2, Feb. 2000, pp. 931–934.

Cowan, T.E., et al., "High Energy Electrons, Nuclear Phenomena and Heating in Petawatt Laser–Solid Experiments," UCRL–JC–133031 Preprint, Jan. 15, 1999, 13 pages.

Cowan, T.E., et al., "Low–Emittance Monoenergetic Electron and Ion Beams From Ultra–Intense Laser–Solid Interactions," UCRL–JC 138049, Submitted to World Scientific, Mar. 16, 2000, 22 pages.

Hojo, H., et al., "Particle acceleration and coherent radiation by subcycle laser pulses," Nuclear Instruments & Methods in Physics Research, A 410, 1998, pp. 509–513.

Cowan, T.E., et al., "Photo–Nuclear Fission from High Energy Electrons from Ultra–Intense Laser–solid Interactions," UCRL–JC–137795, Jul. 13, 1999, 15 pages.

Rau, B., et al., "Strongly Nonlinear Magnetosonic Waves and Ion Acceleration," American Institute of Physics, vol. 5, No. 10, Oct. 1998, pp. 3575–3580.

* cited by examiner

*Primary Examiner*—Nikita Wells
*Assistant Examiner*—Anthony Quash
(74) *Attorney, Agent, or Firm*—Eddie E. Scott; Alan H. Thompson

(57) ABSTRACT

A laser driven compact ion source including a light source that produces an energy pulse, a light source guide that guides the energy pulse to a target and produces an ion beam. The ion beam is transported to a desired destination.

37 Claims, 5 Drawing Sheets

LASER DRIVEN COMPACT ION ACCELERATOR

CROSS-REFERENCE TO RELATED APPLICATIONS

Related subject matter is disclosed and claimed in the following commonly owned, copending, U.S. patent application Ser. No. 09/757,150, filed Jan. 8, 2001, titled "LASER DRIVEN ION ACCELERATOR." U.S. patent application Ser. No. 09/757,150, filed Jan. 8, 2001, titled "LASER DRIVEN ION ACCELERATOR" is incorporated herein by this reference.

The United States Government has rights in this invention pursuant to Contract No. W-7405-ENG-48 between the United States Department of Energy and the University of California for the operation of Lawrence Livermore National Laboratory.

FIELD OF THE INVENTION

This invention relates to methods and apparatus for accelerating particles and, more particularly, to a compact laser driven ion accelerator.

BACKGROUND

Methods and apparatus for accelerating particles have many uses, for example, conventional radiation therapy utilizes electron beams and x-rays as a means of treating and controlling cancer.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a laser driven compact ion source. A light source means produces an energy pulse. A light source guide means guides the energy pulse to a target and produces an ion beam. The ion beam is transported to a desired destination. The method of producing a laser driven compact ion source includes the steps of producing high power, short laser pulses; guiding said energy pulses to a target for producing an ion source; and transporting the ion source to a destination.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1A:
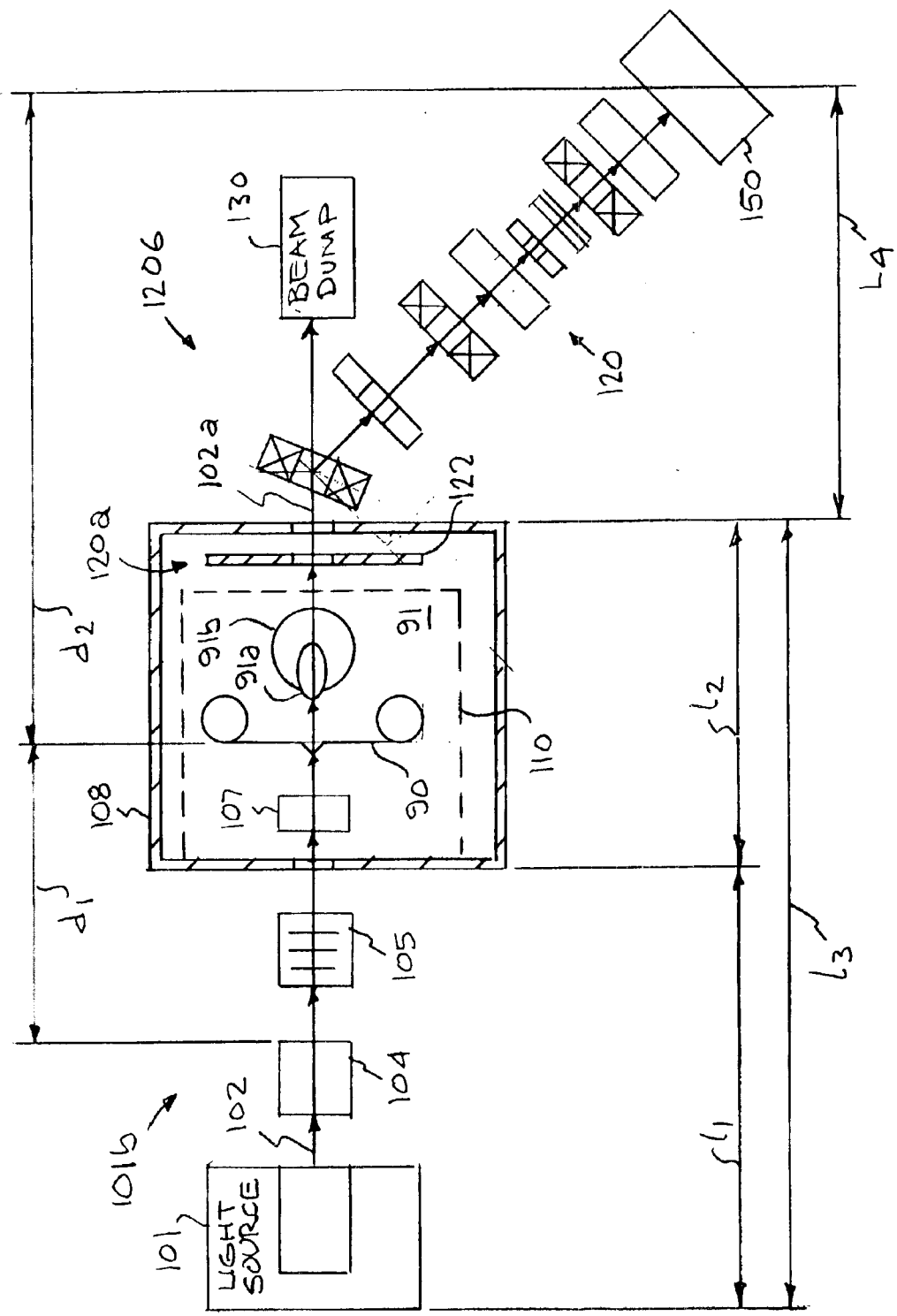
FIGS. 1A–1C provide schematic diagrams illustrating an accelerator system.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Methods and apparatus for accelerating particles have many uses, for example, conventional radiation therapy utilizes electron beams and x-rays as a means of treating and controlling cancer. Other examples of use of accelerator systems and methods described herein include radiation oncology; ion radiology; ion isotope sources; pion, muon, and neutrino beams sources; and spectroscopic diagnosis (nondestructive or otherwise) of different types of materials.

Figure 1B:
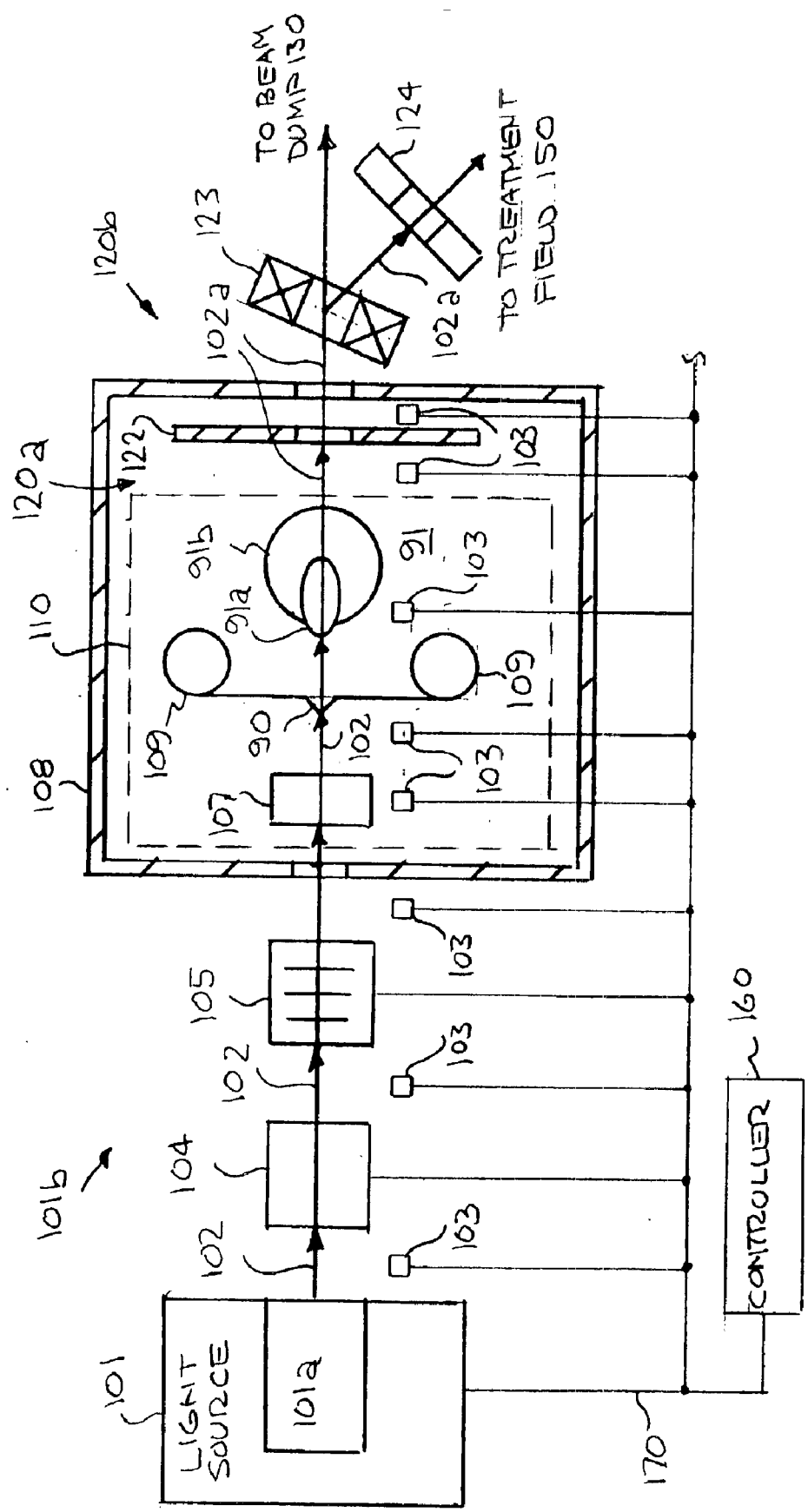
Figure 1C:
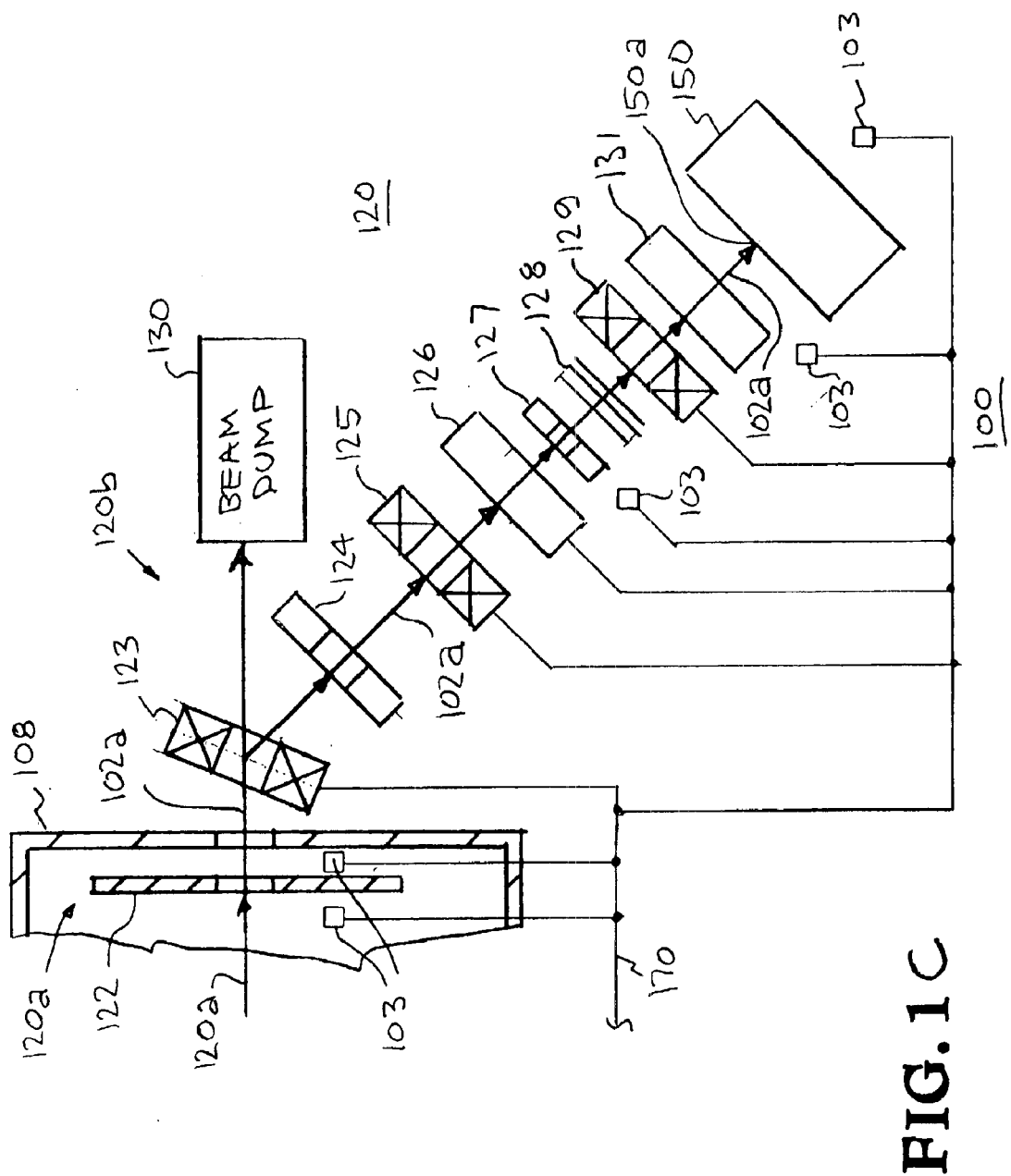

FIGS. 1A, 1B, and 1C illustrate schematic views of an accelerating system 100. The accelerating system includes a light source or laser system 101 producing an energy pulse 102 which travels through a light source guide system 101b to a target system 110 located in a vacuum chamber 108. The pulse 102 strikes the target 90 in the target system 110 and an ion beam 102a is produced which travels through an ion beam transport system and irradiation system 120 to a treatment field 150.

The operation of the accelerating system 100 is controlled by a controller 160 and feedback system 170. These components may combine to form a compact accelerating system. The length, L1, of the light source system 101 and light source guide system 101b may be in the range of approximately 1 to approximately 2 meters. The length, L2, of the target system 110 and a first section 120a of the ion beam transport and irradiation system 120 may be in the range of approximately 1 to approximately 2 meters. Therefore, the overall length of the light source system 101, light source guide system 101b, the target system 110 and a first section 120a of the ion beam transport and irradiation system 120, L3, may be in the range of approximately 2 to approximately 4 meters. The length, L4, of separation of the vacuum chamber 108 and the treatment field (or object) 150 may vary depending on the specific application. For example, L4 may range from approximately 0.25 to approximately 10 meters. It is to be understood that these exemplary lengths may vary higher or lower, again, depending on the specific application.

The accelerating system 100 is controlled by a controller 160 whose functions will be described in detail below. In order to maximize a flux of ions produced in the accelerator system 100, a chirped-pulse amplification (CPA) based, compact, high-repetition, high fluence laser system (e.g., a Ti: sapphire laser) may be utilized as a light source system 101. The basic configuration of such a light source system 101 is described in U.S. Pat. No. 5,235,606, issued Aug. 10, 1993 to Mourou, et al., which is hereby incorporated by reference. The light source system 101 having a pulse shaper 101a emits an energy pulse (or pulses) 102 having a pulse energy of approximately 1 to approximately 10 Joules (J). The pulses 102 may be delivered at a rate of approximately 0.1 to approximately 100 Hertz (Hz). The pulses 102 are transported by a light source guide system 101b which may include a series of mirrors 104 and thin foils 105. Mirrors 104 are configured to guide and focus the pulse 102 with a predetermined intensity using the last mirror in the mirror series 104. Before the pulse 102 enters the target system 110, the light source guide system 101b may include a series of thin foils (e.g., metal) 105 that are capable of controlling or reducing the prepulse of each pulse 102. The prepulse section of each pulse 102 may comprise a field of the pulse 102 prior to the arrival of the main peak of the pulse 102. Because a pulse 102 may be very short and intense, even a fraction of the peak intensity of the pulse 102 (e.g., the prepulse) may be sufficient to ionize and/or ablate the foils 105. The prepulse may be controlled by using multiple foils 105 and a pulse shaper 101a in the light source system 101. The pulse shaper 101a may optionally include a frequency multiplier.

Controller 160 and feedback system 170 are configured to perform monitoring, controlling and feedback functions for the accelerator system 100. Controller 160 may be a microprocessor or other conventional circuitry. A plurality of sensors 103 monitor the intensity of the pulse 102 and ion beam 102a throughout the accelerator system 100. As illustrated by FIGS. 1B and 1C, monitoring points where sensors 103 are positioned may include the light source system 101 output, mirror series 104 output, the target entry point of the pulse 102, after the target 90, before slit 122, before magnets 123, after filters 126, and before and after the treatment field 150. In alternative embodiments, it is to be understood that sensors 103 may not be limited to these numbers or positions. The monitoring information is forwarded through the feedback system 170 to the controller 160. Based on this input, controller 160 is configured to fine-tune the light source system 101 and may provide control signals to light source 101, mirror series 104, foils 105, magnets 123, 125, 129 and filters 126 to adaptively control the quality of pulse 102 and ion beam 102a. Parameters of the pulse 102 and ion beam 102a which may be adaptively controlled by the controller 160 and the feedback system 170 may include repetition rate, laser flux, focus, aperture, angle, intensity, and pulse length.

The pulses 102 may be guided by a light source guide system 101b into vacuum chamber 108 which encloses target system 110. The target system 110 may be composed of prefoils, target feed, slits and shields represented by reference numeral 107 and a target 90. (Target 90 may also be referred to herein as a foil, a film, a source and accelerator element, or an interaction element). Pulses 102 may be intense, ultrafast (i.e., having a pulse length between approximately 1 to 500 femtoseconds (fs)) and ultra-relativistic. During operation, the pulses 102 immediately (within a few fs of the pulse entry to the target 90) and substantially destroy the target 90 and ionize multiple electrons per each of the atoms contained in the target 90 to form "hot" electrons. Hot electrons may be defined as electrons having energy greater than approximately 1 MeV. Together with conduction band electrons, these hot electrons form a high density electron cloud 91b in region 91 that is driven forward by the acceleration and heating of these electrons to high energies by the light source system 101. An electrostatic field is set up through charge separation by these hot electrons. Therefore, according to a simple one-dimensional model, an accelerating gradient $E_0$ is wavelength, $\lambda$, proportional to the energy (or temperature) of hot electrons divided by the width of the charge separation, which is approximately the Debye length $\lambda_D$ of hot electrons:

$$E_0 = \alpha T_h / \lambda_D,$$

where $\alpha$ is a constant (about 5 to 10) and $T_h$ is the energy of hot electrons. The energy gain of ions may be the following:

$$E_1 = q l E_0,$$

where q is the ion charge and l is the acceleration distance. Therefore, $$E_1 = \alpha q (l/\lambda_D) T_h.$$

When l is approximately $\lambda_D$, which is the case for a simple one-dimensional geometry, an energy gain of ions is obtained as $$E_1 = q l E_0.$$

Based on these equations, the acceleration system 100 is designed to enhance $E_1$ by increasing $\alpha$, $1/\lambda_D$, and $T_h$ (and except for protons, q also).

For example, when the geometry of the target 90 has a substantially concave geometry, both $\alpha$ and l may be increased. If electrons are heated or accelerated to higher energy, $T_h$ (or even $T_h/\lambda_D$) increases. This is because $\lambda_D$ is proportional only $T_h^{1/2}$. The changing target parameters (which are discussed in detail below) may increase $\alpha$, l or $T_h$, or all of these.

During operation, the energy of the light source system 101 may be compressed into an ultrashort time scale of approximately 10 to 100 fs after a CPA's time stretcher and compressor (not shown), but before the final focal mirror in the mirror series 104. The final focal mirror in the mirror series 104 may focus the pulse 102 which has been time-compressed into a spatially compressed light spot on the target 90 in the target system 110. The distance, d1 (as shown in FIG. 1A), from the final focal mirror in the mirror series 104 to the target 90 may be substantially less than 1 meter (m).

The light source system 101 is capable of delivering to the target 90 a light beam intensity in the range of approximately $10^{18}$ to $10^{23}$ Watts (W)/centimeter (cm)$^2$, with approximately $10^{21}$ W/cm$^2$ being the typical intensity. The target system 110 is designed to allow the optical interaction of the intense short pulse 102 with the target 90 to yield a high flux of energetic ions such as protons 91a (as shown in FIG. 1B). As discussed above, the target 90 may be substantially destroyed when struck by the pulse 102, forming a plasma 91b containing electrons and ions (e.g., protons 91a) in region 91. The plasma electrons may then be driven towards the first section 120a of the ion beam transport and irradiation system 120 and the plasma electrons may pull ions with them towards the first section 120a. The distance from the target 90 to the treatment field 150, d2, may also be less than approximately 1 m. Therefore, the combination of distances d1 and d2 may be less than approximately 1 m. The target 90 may be a film or foil that is rolled into position on rollers 109 under control of controller 160 for each shot of the light source system 101. The target 90 may include a target portion and a prepulse controller portion which controls the prepulse of the pulse 102 or reduces it. Both target portion and prepulse controller portion may be moved synchronously with the pulse shots from light source 101 to expose a fresh film surface. The target 90 will be discussed in further detail below.

The first section 120a of the ion beam transport and irradiation system 120 is located inside vacuum chamber 108. The second section 120b of the ion beam transport and irradiation system 120 is located between the vacuum chamber 108 and the treatment field 150. The first and second sections 120a, 120b of the ion beam transport and irradiation system 120 may include slit 122, magnet or magnets 123, beam dump 130, shields 124, magnet or magnets 125, filter or filters 126, aperture or apertures 127, foil or foils 128, magnet or magnets 129, optional electronic guide 131 and sensors 103. The first and second sections 120a, 120b may include other transportation and control elements not shown in FIGS. 1A–1C. Second section 120b may optionally include a support of the treatment field 150 for irradiation of a patient (support is not shown) in oncological applications.

The ion beam transport and irradiation system 120 is configured to discriminate among various radiation components produced by the pulse 102 striking the target 90. The ion beam transport and irradiation system 120 is designed to achieve this discrimination by isolating predetermined energy ions which are to be used in irradiating the treatment field 150 and separating (i.e., dumping) the radiation components which are not to be used in the irradiation on the treatment field 150. The radiation components which result from the pulse 102 striking the target 90 include different species of ions (e.g., protons), x-rays, electrons, remnants of the pulse 102, and different energy components (e.g., MeV, 10's MeV, and 100's MeV within a certain energy band or window). After ion generation from the target 90, ions such as protons 91a with a predetermined emittance are allowed to pass through the slit 122 in the form of an ion beam 102a. Beyond the slit 122, magnets (or magnet) 123 are designed to discriminate the energy of the predetermined protons (and other types of radiation) by bending the different species and components of radiation and directing the remaining portion of the ion beam 102a into beam dump 130. The magnets 123 may be pulsed as well as electronically modulated for control as well as for scanning. Combined with the magnets 123 are shields 124 and filter or filters 126 which may also be used not only to protect undesired radiation from hitting the treatment field 150 for irradiation, but also to define and discriminate a predetermined portion of the phase space of the given radiation component to be delivered to the treatment field 150. A beam aperture 127 may be used to control the size of the beam 102a to irradiate the treatment field 150. A plurality of high Z metallic foils 128 may be configured inward to stop low energy or low ranged components of radiation and monitor the ion beam 102a. Magnet(s) 129 may control the direction of the ion beam 102a. An optional electronic guide 131 may be placed after the magnet(s) 129 to perform a scanning function of the ion beam 102a on the treatment field 150.

The width, angle and emittance of the ion beam 102a which strikes the treatment field 150 is controlled by a combination of accelerator system 100 design choices. These design choices may include the nature of the target 90 (which will be discussed in detail below), the light source system 101 intensity and focus, the distance of the light source system 101 from the target 90, the choice of transport elements (e.g., magnets, filters, foils, shields, mirrors, and slits), the width of the beam aperture 127, and the use of an optional electronic guide 131. The size of the light source (e.g., laser) spot 150a on the treatment field 150 may vary from about 0.5 to about 20 $cm^2$ in area in accordance with accelerator system 100. For example, a pointed, small emittance beam (i.e., a pencil beam producing a light source spot 150a of approximately 0.5 to approximately 2 $cm^2$) on the order of approximately 1 millimeter milliradians (mm mrad) may be produced by the accelerator system 100. Such a small pencil beam may be configured to scan through the electronic guide 131 and cover a portion of or the whole region of the treatment field 150 by scanning in a predetermined pattern where irradiation is desired. Therefore, in oncological applications, a small tumor (i.e., in the range of approximately 5 to 20 cm) may be more accurately targeted for localized or conformal treatment.

The optical elements (e.g., mirror series 104), target 90, the magnets 123, 125, and 129 and other transport elements may be controlled adaptively through the controller 160 and feedback system 170 during and after each shot from light source system 101. Through the use of the controller 160 and feedback system 170, the control and modulation of the beam energy, energy band, size, and repetition rate may be achieved—shot by shot—of the light source system 101. The ion beam transport and irradiation system 120 may also be configured to discriminate a portion or portions of the ion beam 102a in angle and size to adjust the beam's size, emittance, and flux for predetermined ion beams 102a which allows for a highly flexible system.

At least four parameters of the target 90 may be varied to obtain a change in performance of the ion beam 102a which strikes the treatment field 150. These four parameters may include the width, material, geometry (or shape) and surface of the target 90. The modification of these parameters allows for the maximization of the interaction of the pulse 102 and the target 90 and the maximization of the energy and flux of the ion beam 102a which results from the pulse 102 striking the target 90. A detailed discussion of the four parameters follows.

The pulse 102 which strikes the target 90 has a field (e.g., laser field) with an intensity in the ultra-relativistic region. In the ultra-relativistic region, the electron momentum in the field exceeds mc, where m is the electron rest mass and c the speed of light, so that the electron energy in the field far exceeds that of electron rest mass (e.g., at least approximately $10^{21}$ $W/cm^2$). The pulse 102 may be irradiated over a small spot 90a (e.g., approximately 2 to approximately 10 square microns) on the target 90. The target 90 acts as an ion source as well as an accelerator, emitting energetic ions (e.g., protons 91a as shown in FIGS. 1A–1B) in the plasma region 91 behind the target 90. As discussed above, the plasma region 91 is followed in sequence by the ion beam transport and irradiation system 120 which may extract a predetermined band of protons 91a from the plasma region 91. The beam 102a which emerges from the ion beam transport and irradiation system 120 will be an ion (e.g., proton) beam and is capable of irradiating the treatment field 150 of a patient.

The compact electron accelerator using a laser accelerates electrons to 10's of MeV in less than a centimeter. This method is sometimes called the Laser Wakefield Accelerator (LWFA), as the laser pulse excites a wakefield which accelerates electrons. The compact acceleration of ions to velocities comparable to the speed of light proves to be more difficult due to their heavy mass. While electrons can be, at least after a short pre-acceleration, accelerated with traveling electromagnetic waves, ions take much more energy (and thus much more time and distance) before electromagnetic radiation can be used for further acceleration. Thus, ion accelerators to date use static electric fields for their (incoherent) pickup and pre-acceleration of particles or similar methods. Only once the ions reach velocities comparable to the speed of light, the pre-accelerated particles are coupled to linear accelerators for further acceleration. The state of the art ion injectors and accelerators are therefore of much greater spatial extent than their electron counterparts. The large initial electrostatic acceleration calls for a machine usually more than a meter long just for the injector. Further acceleration requires an even larger apparatus. The room, weight, and cost for the conventional accelerators are so substantial that only large dedicated facilities can handle these.

Figure 2:
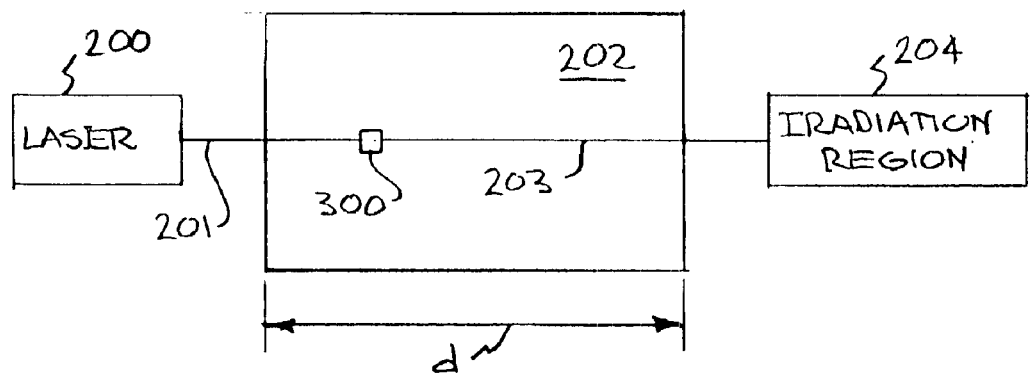
FIG. 2 is a schematic diagram of a layout of a laser-driven ion source and accelerator system of the present invention.

The embodiment shown in FIG. 2 illustrates a layout of a laser-driven ion source and accelerator system. More particularly, the embodiment is a compact, laser-induced pickup and acceleration of plasma ions to mildly relativistic energies. Compared to the current technology, this embodiment allows an ion source of a longitudinal extent of only a few centimeters rather than meters. Recognizing the need for a compact ion accelerator, it is the general goal of this first embodiment to provide a novel ion pickup and acceleration scheme not based on electrostatic pre-acceleration of ions. The new acceleration scheme is small in physical size (order of centimeters) and cheap when compared to conventional ion accelerators in use. Therefore a high power, short laser pulse may be used together with a thin, dense layer of plasma bordered by another short, rarefied, and magnetized layer of plasma to achieve such an acceleration of ions.

The major components of the system include a laser apparatus 200, an ion accelerator 202 and an object to be irradiated 204. (For the purposes of this disclosure, components of the system not useful in demonstrating the principles of the invention have not been shown).

Figure 3:
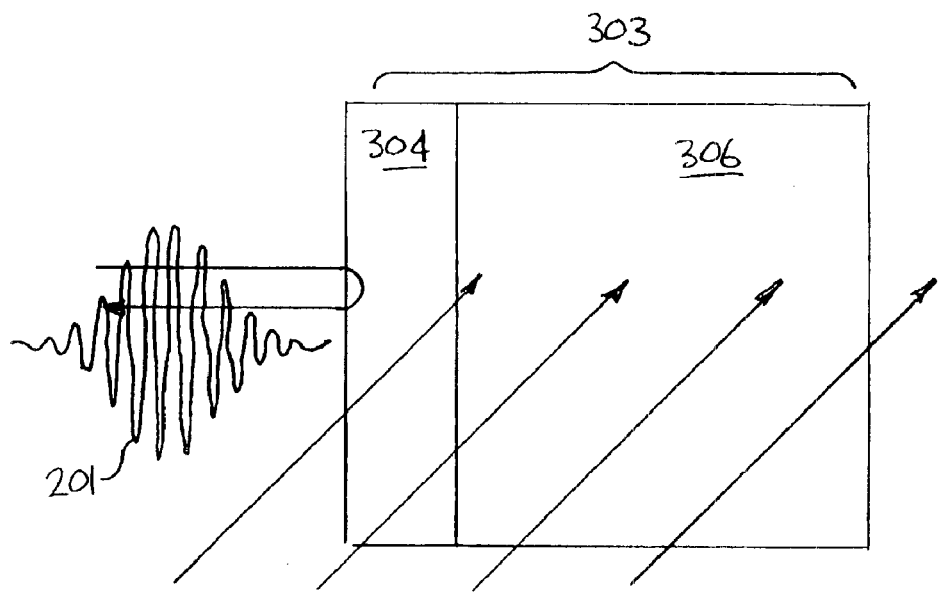
FIG. 3 illustrates the plasma density in the ion accelerator.

FIG. 3 discloses the plasma density in the ion accelerator 202. The use of a high power, short laser pulse 201 together with a first thin, dense layer of plasma 304 bordered by a second short, rarefied and magnetized layer of plasma 306 to achieve such an acceleration of ions. As the laser pulse reflects off the optically thick part of plasma layer 304, it transfers its momentum onto the motion of the plasma particles, i.e., plasma electrons and ions. A fast spatial decrease of the plasma density allows for the generation of a coherent motion of particles inside the rarefied, magnetized plasma 306. A proper tuning of the plasma parameters results in a fast, short, and dense ion plasma wave. The ions that make up this wave can be decoupled after the initial acceleration and thus can serve as an ion source. This mechanism allows for the generation of fast ion waves, their decoupling from the background plasma, and their use as a coherent source of mildly relativistic ions.

FIG. 3 shows the short, intense laser pulse 201 incidents a thin layer of overdense plasma ($\omega_{p,local} > \omega_1$) and is reflected off this surface while transferring about twice its momentum onto the plasma particles. This momentum is carried through the overdense plasma layer and reaches its far side, at which a magnetically underdense plasma 306 ($\Omega_{ce} > \omega_{p,local}$) converts the incoherent momentum into a coherent ion wave. Finally, once this ion wave with its fast ions has formed, decoupling of those ions from the bulk plasma provides the ion source.

A direct employment of the laser-driven electron acceleration through the method of the LWFA for the laser-induced injection (pre-acceleration) of ions into an acceleration structure requires a dimensionless laser field strength parameter $A_0 = (eE_1)/(M_i\omega_1 c) = O(1)$. Here, $E_1$ is the peak value of the laser light electric field strength, $M_i$ is the ion mass, and $\omega_l$ is the frequency of the laser light. At the typical laser light wavelength of high power lasers of about 1 µm, this amounts to intensities of the order of $O(10^{18} \text{W/cm}^2)$. For current and probably future high intensity laser systems, such field intensities are difficult to achieve.

In order to efficiently utilize laser pulses for the pickup of ions from the bulk plasma, the laser pulses momentum must be efficiently transferred to a small amount of select ions. A "small amount of ions" may defined by the relation $P_1 = \eta_{eff} P_{ions} = \eta_{eff} N P_{ion}$, where the laser pulse momentum $P_1$ is equated to the final momentum of the ions $P_{ions}$, times some coupling efficiency $0 \leq \eta_{eff} \leq 100\%$. The total number of ions N that are accelerated must thus be small in order to achieve a relativisticaly high individual ion momentum $P_{ion}$.

A momentum transfer from the pulse 201 to the plasma is maximally achieved when bouncing the laser pulse off an overdense layer of plasma 304 such that substantially twice the initial laser pulse momentum will be converted into particle motion. The plasma 304 is overdense if the local plasma frequency $\omega_p = \sqrt{4\pi n_1 e^2/m}$ is greater than the laser frequency $\omega_1$. Here, $n_l$ denotes the local background plasma density and $m_e$ and $-e$ are the electron mass and charge, respectively. Furthermore, a complete reflection of the laser pulse is ensured for a plasma layer of at least one collisionless skin depth $c/\omega_p$ thickness, c being the speed of light. An upper limit of the individual ion momentum when transferring the laser pulse momentum into the overdense plasma motion can be estimated as the following:

$$\frac{P_{ion}}{M_i c} = \gamma_i \beta_i = 2 \frac{I_i \sum \tau \eta_{eff}}{M_i c^2 N}$$

where $\Sigma$ is the transverse area irradiated by the laser pulse, L the longitudinal length of the plasma slab (with $c/\omega_p$ as its lower limit), $\tau$ the duration of the laser pulse, and $M_i$ and $m_e$ the ion and electron mass, respectively. Since highly intense laser pulses have durations $\tau\omega_1 = O(10^1-10^2)$ at normalized field strengths $a_0 = O(1)$, the resulting normalized ion momentum remains non-relativistic ($=\gamma_i \beta_i <<1$).

For this reason, a relatively small amount of ions must be accelerated by the same laser pulse. In order to accomplish that, a coherent ion motion inside a rarefied plasma 306 ($\omega_{p,local} << \omega_1$) needs to be exited due to the irradiation of an overdense plasma 304 by the short, intense laser pulse 201. Coherent ion plasma waves can be excited in unmagnetized as well as in magnetized plasmas. Since the wave velocities of waves in a magnetized plasma may be selected by controlling external parameters and since these waves are in general much faster than those of the unmagnetized ones (and since the resulting fast ion should gain relativistic velocities), the rarefied part of the plasma is chosen to be magnetically underdense, i.e. $\Omega_{ce} \geq \omega_{p,local}$. Here, $\Omega_{ce} = (eB_1)/(m_e c)$ is the electron cyclotron frequency with $B_1$ being the external magnetic field strength. For given field strengths $B_1$, this sets an upper limit on the density of the rarefied plasma 306.

The ions that make up the ion wave, however, do not necessarily move at the wave phase velocity. In fact, as discussed below, the single ion velocity and ion wave phase velocity coincide only for highly nonlinear wave modes. Therefore, one has to excite a strongly nonlinear, fast ion wave through the laser-plasma interaction. The necessary laser, plasma, and magnetic field strength parameters are given below.

Also, since the overdense plasma 304 mainly serves to stop and reflect the laser pulse, it must be chosen thick enough in order to completely reflect the pulse, but still thin enough to ensure an efficient momentum transfer from the initial laser pulse onto the nonlinear ion wave in the rarefied plasma 304. The appropriate thickness of the plasma will be discussed below.

Ion Waves

The nonlinear ion wave can be described by a two fluid model with cold electrons and ions. The relevant equations for the motion of the electron and ion fluids in a frame moving with the ion wave can be derived from the equations of motion and the momentum and energy conservation laws for arbitrary external magnetic field strengths with the assumption of light electrons ($m_e/M_i \ll 1$). An ion wave moving along the x direction inside a constant, external magnetic field $B_1$ along the z-direction. Conservation of momentum and energy then yields the following relations between the ion fluid velocities and the electric and magnetic fields The ion wave propagates alone the x-direction with a velocity $V_1$ and the x- and y-velocities of the ion fluid $v_{ix}$ and $v_{iy}$ are normalized to this speed. The Mach number of the ion wave $M_A = V_1/V_A$ is defined as the ratio of ion wave speed $V_1$ and the Alfven velocity $V_A = B_1/\sqrt{4\pi n_1 M_i}$. Here, $n_1$ is the background density of plasma electrons.

The Mach number $M_A$ is limited to values $1 \leq M_A \leq 2$ and the maximum velocity of the ions in the laboratory frame along the direction of propagation (x-direction) is $$V_{ix,m} = V_1\left(2 - \frac{2}{M_A}\right),$$

with $V_{ix,m}$ being the real velocity of the ions. Thus, ions within a weakly nonlinear ion wave ($M_A \gtrsim 1$) barely pick up any speed while ions of a strongly nonlinear wave ($M_A \lesssim 2$) can move with velocity close to the wave speed itself.

The individual ion speed can be controlled by a judicious choice of the background magnetic field $B_1$ and the electron plasma density $n_l$ provided that the Mach number $M_A$ of the ion wave can be accurately controlled. For this, the total momentum of the finite ion wave may be calculated, i.e., including the fluid-like ion and electron motion as well as the self-consistent electromagnetic fields for given parameters $V_A$ and $M_A$, and equate this momentum with twice the incoming laser pulse momentum, modified by a factor $1/\eta_{eff}$. With a momentum coupling coefficient $\eta_{eff}$, an ion wave of arbitrary nonlinearity measured in terms of $M_A$ may thus be constructed.

For a magnetically underdense plasma the total wave momentum $P_\omega$ can be expressed as $$P_\omega \simeq 2.6 \frac{\sum B_1^2}{\pi \omega_{pe} \varepsilon},$$

where $M_A \simeq 2$ was used for the last equation. Thus, an incoming laser pulse with a momentum $$P_i = \frac{I_i \sum \tau}{c} = \frac{P_\omega}{2\eta_{eff}} \simeq \frac{1.3 \sum B_1^2}{\eta_{eff} \pi \omega_{pe} \varepsilon}$$

sets up a strongly nonlinear ion wave with ions that reach a maximum velocity of $V_{ix,m} \simeq V_1 = M_A V_A \simeq 2B_1/\sqrt{4\pi n_1 M_1}$. This, in turn, determines the required intensity $I_1$ for the laser pulse for a coupling efficiency $\eta_{eff}$. The efficiency $\eta_{eff}$ is determined mainly by the thickness of the initial overdense slab of plasma 204. While increasing the longitudinal extent of the plasma slab reduces the transfer of the laser pulse momentum onto the ion wave inside the rarefied plasma 206, the overdense plasma slab 204 must be thick enough to ensure complete reflection of the laser pulse. In other words, a good choice of the initial plasma slab is a thickness of a few $c/\omega_{pe,local}$ only. Numerical simulations show that a coupling efficiency of about 10% can be reached by choosing the thickness to be about $5c/\omega_{pe,local}$. Thus, about 10% of the initial laser pulse momentum can be transformed into a coherent ion wave.

The length of the ion wave can be numerically determined by integrating the equations of motion and finding the half width of the maximum ion motion. In general, higher background electron densities shorten the ion wave to pulse lengths far below 1 cm, but they require high magnetic field strengths in order to magnetize the plasma. For a given background density of the electrons, however, increasing the field strength of the external magnetic field results into faster ion waves, but also into longer widths of the wave.

As the ion wave should be fast in order to accelerate the ions to relativistically high speeds, a short wave is required for two reasons: first to keep the spread of the ions low (i.e. within the length of the ion wave) and second to keep the total volume of magnetized plasma as small as possible. While the first requirement improves the beam quality of the outcoming ion beam, the second is necessary since high magnetic fields of the order of several Tesla can only be produced of a short period of time and a small volume. More importantly, the motion of the ions transverse to the direction of the ion wave should be substantially limited to the transverse spotsize of the initial laser pulse to ensure a rather 1-dimensional setup for a good quality beam. As large laser spotsizes require a high laser pulse energy ($\geq 1$ J) even for moderate intensities ($\sim 10^{16}$ W/cm$^2$), the transverse motion is necessary to remain small. This imposes the minimum limit of the background density to be of the order of $10^{14}$ cm$^{-3}$, which in turn requires the minimum limit of an external magnetic field of the order of 10 T for a fast ion wave.

Figure 4:
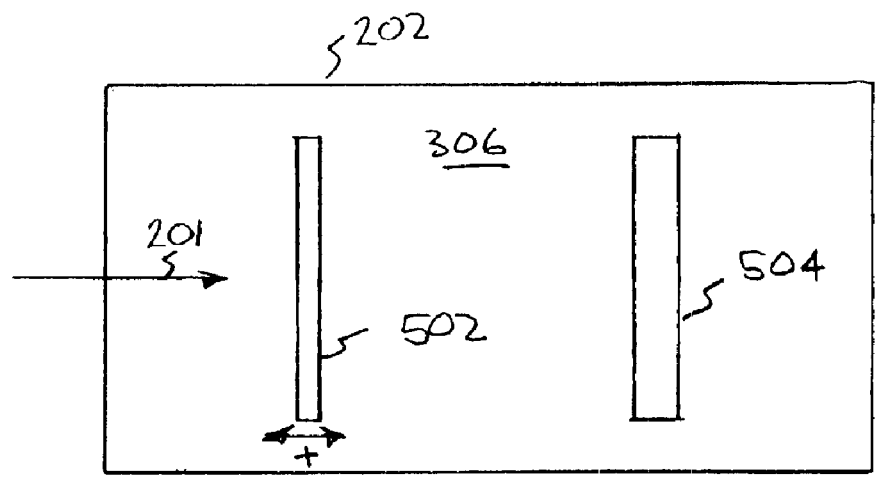
FIG. 4 illustrates a detailed view of the target in the ion accelerator.

For the ion acceleration scheme of this embodiment, the following setup may be used. A thin film of plastic 502 of about 0.1 $\mu$m thick may be used to reflect the laser pulse off its surface and transfer the electromagnetic momentum as illustrated by FIG. 4. If the laser pulse has an intensity of about $10^{14}$ W/cm$^2$ or above, the medium will be ionized and the thin film 502 will turn into a plasma with an electron density of the order of $10^{22-23}$ cm$^{-3}$. For the purpose of ion acceleration, a high power, ultrashort laser pulse is used. These pulses are most easily and compactly achieved with Ti:sapphire, Nd:glass, Cr:LiSAF, and other laser systems which operate at wavelengths around 1 $\mu$m. Thus, the plasma generated from the thin film is overdense $\omega_{p,f} > \omega_l, \omega_l$ being the laser frequency and $\omega_{p,f}$ the plasma frequency inside the film) with respect to the laser light and, a plasma layer of at least one collisionless skin depth $c/\omega_{p,f}$ thickness, c being the speed of light. Furthermore, these laser systems can operate at intensities exceeding $10^{14}$ W/cm$^2$ by many orders of magnitude and are hence far above the threshold of ionization. For these laser systems, the thin film 402 indeed instantly turns into an overdense layer of plasma. Bordering the far side of the thin film, a rarefied plasma 306 of a longitudinal extent of a few centimeters is placed. This rarefied plasma 306 has an equilibrium electron density of about $10^{14}$ cm$^{-3}$ such that this plasma can be magnetized ($\Omega_{ce} > \omega_{p,local}$) without excessive external magnetic field strengths. Methods of providing this rarefied plasma 306 ranges from the laser ablation of the far side of the film surface to a pre-contained gas plasma. There is no need for an exact parameter match for this plasma 306. The required external magnetic field for the generation of a magnetically underdense plasma ($\Omega_{ce} \geq \omega_{p,local}$) can be expressed as $$B_1[T] \geq 3.2 \cdot 10^{-7} \sqrt{n_1[cm^{-3}]}.$$

This condition limits the plasma density in an attempt to make the external field not exceedingly large (typically, several Tesla).

As discussed above, the transverse motion of ions should not exceed the initial laser spotsize $w_0$. An estimate for the distance traveled transversely to the direction of the ion wave propagation leads to a critical density $n_{crit}$ defined by $$n_1 \geq n_{crit} \approx \frac{\beta_1^4}{\omega_0^2[\mu m]} 1.3 \cdot 10^{22} \text{ cm}^{-3}$$

with $n_1$ being the background plasma density of the rarefied plasma. Thus, for large laser spot sizes ($\omega_0 \sim 100 \mu m$) and mildly relativistic wave speeds ($\beta_1 = V_1/c \sim 0.1$), the background density can be as low as $10^{14}$ cm$^{-3}$ before two-dimensional effects become important.

The required laser pulse energy can be found by equating the ion wave momentum with twice the incoming laser pulse momentum multiplied with some assumed momentum coupling efficiency $\eta_{eff}$ and deriving the necessary light pulse energy. The necessary laser pulse energy is described by the following:

$$E_{laser}[J] \simeq \frac{B_1^2[T] \omega_0^2[\mu m]}{\sqrt{n_1[cm^{-3}]} \eta_{eff}}.$$

Thus, for the parameters mentioned above ($n_1 \sim 10^{14}$ cm$^{-3}$, $\omega_0 \sim 100 \mu m$, $B_1 \sim 10$ T, $\eta_{eff} \sim 10\%$), the laser pulse energy is of the order of one Joule.

Assuming a laser spotsize of $\omega_0 = 100 \mu m$ and a momentum coupling efficiency $\eta_{eff}$ of about 10%, the laser pulse energy required to set up a strongly nonlinear solution is in the range of 0.1–10 J. In order to operate in a quasi one-dimensional regime, the background density must be higher than the density $n_{crit} \sim 10^{14}$ cm$^{-3}$. For kinetic ion energies of the order of 10 MeV and higher, one thus has to use a total laser pulse energy of about 1 J and an external magnetic field of the order of 10 T.

The laser pulse length is restricted by the fact that the duration of the laser pulse should be much less than the one of the ion wave in order to ensure efficient momentum coupling. Since the ion wave duration is of the order of the ion plasma frequency $\omega_{pi} = \epsilon \omega_{pe}$ for fast ion waves, the condition reduces to $$\tau_{laser} \ll \left( \frac{1}{\omega_{pi}} \right) \simeq \frac{8 \cdot 10^{-4}}{\sqrt{n_1[cm^{-3}]}} s$$

for a hydrogen plasma. For local background densities of $10^{14}$ cm$^{-3}$, the laser pulse should be much smaller than about $10^{-10}$ s, a requirement which may be achieved with current femtosecond laser technology. Therefore, this embodiment may use a laser pulse with a short but still relatively simply realizable duration ($\geq 100$ fs). Together with the laser pulse energy relation and the assumed spotsize, the required intensity of the pulse is thus $\sim 10^{16}$ W/cm$^2$.

In order for the coherent ion wave to decouple from the background plasma and turn into a beam of freely propagating ions, the support of the ion wave must be cut non-adiabatically. Thus, within a distance that is comparable to the ion wave half width ($c/\omega_{pi} \sim 2$ cm), the external magnetic field must decay from its peak value ($\simeq 10$ T) to a low one. An upper limit for the final magnetic field is found by certifying that the local gyroradius of the energetic ions in this field should be much smaller than the typical scale length of the accelerator. With this requirement, we find the value of the "background" magnetic field to be less than about 1 T. This requirement should not pose a serious constraint on the experimental realization.

The decoupled ions now freely streaming forward are, however, subjected to plasma instabilities and thus to additional particle beam distortions and energy loss unless the background plasma is of finite extent such that the ion beam can escape the bounded plasma. It is therefore suggested to keep the rarefied plasma confined between the initial thin layer of plastic that is responsible for bouncing off the laser pulse (as shown in FIG. 3) and another such layer at the far end of the apparatus.

Thus, this embodiment's parameters are summarized as follows. The plasma should be approximately a 0.1 $\mu m$ thick plastic film bordering an approximately 4 cm long rarefied plasma 206 at a plasma density of $10^{14}$ cm$^{-3}$. The rarefied plasma 306 may be confined by a second plastic film at the far end in an alternative embodiment. The entire plasma is magnetized with an external magnetic field of about 10 T. This magnetic field decays within a distance of the order of centimeters behind the far edge of the rarefied plasma to a value far below 1 T. Alternatively, the entire magnetic field can decay to a small background value much less than 1 T within a time of the order of one nanosecond or a combination of spatial and temporal reduction of the external magnetic field can be chosen. The laser pulse is a 100 fs long laser pulse to form a Ti:Sapphire or similar laser system with about 1 J pulse energy and a radial spotsize of about 100 $\mu m$ is focussed onto the plastic film.

Aside from the required laser energy and laser pulse length discussed above, the number of accelerated ions and their average kinetic energy can be determined by scaling laws as well. For the ion number N, one can find $$N \simeq n_1 \sum \frac{c}{\omega_{pi}} \simeq 0.2 \omega_0^2[\mu m] \sqrt{n_1[cm^{-3}]}$$

where A again is the transverse area approximated by the square of the laser spotsize $\omega_0$. In the non-relativistic regime ($\beta_1 \ll 1$), the individual kinetic energy of the accelerated ions is expressed as $$E_{ion} \simeq \frac{1}{2} M_i (2V_A)^2 \simeq \frac{B_1^2[T]}{n_1[cm^{-3}]} 10^{19} eV$$

This scaling, in the non-relativistic regime, is independent of the individual ion mass. However, the ion speed becomes slower for heavier ions.

From this and the parameters discussed above, the resulting parameters of the ion beam may be estimated. For a short (approximately 100 fs), intense (approximately $6 \cdot 10^{16}$ W/cm$^2$) laser pulse with a spotsize $\omega_0$ of 100 $\mu m$ and a total pulse energy of 1 J, a strongly nonlinear ion wave may be generated with a wave speed $V_1 \simeq 2V_A \simeq 0.15$ c in a rarefied ($10^{14}$ cm$^{-3}$), magnetized ($B_1 \simeq 10$ T) hydrogen plasma. Such a high Mach number wave then produces about $10^{10}$ protons at energies of about 15 MeV.

Figure 5:
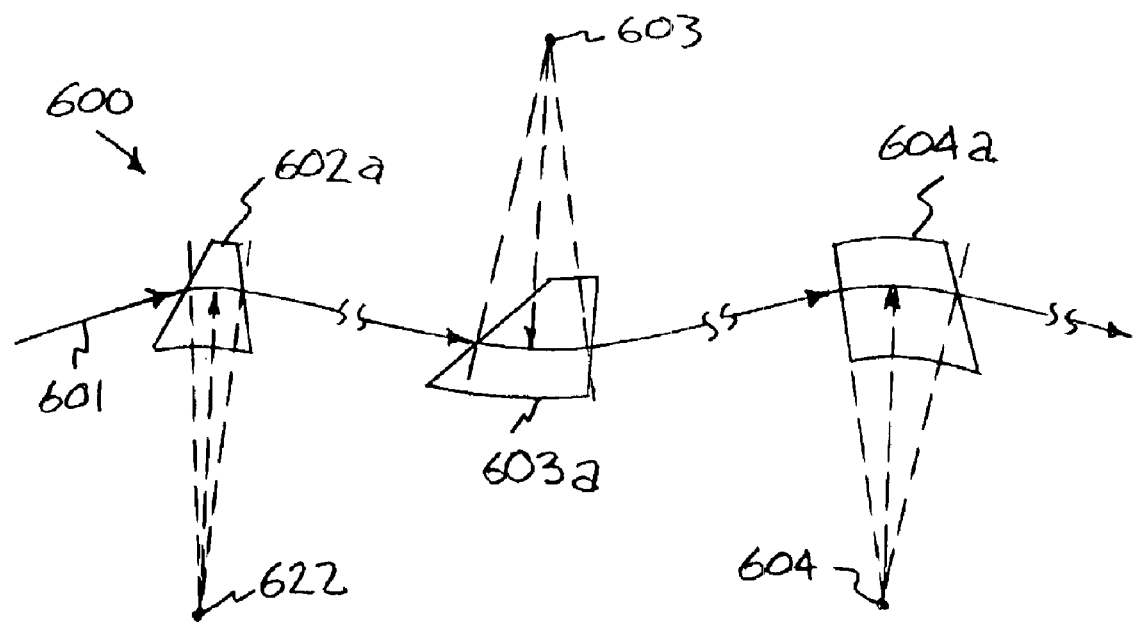
FIG. 5 illustrates an extraction magnet system.

Referring now to FIG. 5, an extraction magnet system, generally designated by the reference numeral 600, is shown. The magnet system 600 extracts, collimates, and directs the generated ion beam 601. The magnets 602, 603, and 604 are used to make acceptance of energetically broad spectrum of beams and transport them to the site of irradiation in a compact and achromatic fashion. The site of irradiation, for example, can be a patient.

The ion accelerator of this embodiment allows for ion accelerators that are compact (~1 m) and relatively inexpensive for energies in excess of 10 MeV. Without the final component for acceleration this embodiment embodies very compact (a few cm) and cheap ion pickup systems or components that can be a part of other systems. The driving laser technology is readily available and may sit on a table top since it is not excessively heavy. Thus, the total system can be small and not heavy. The overall construct is also an order of magnitude less expensive than the conventional ion accelerators. These features include the following:

1) producing a laser induced ion source;
2) producing a coherent ion source;
3) producing a sub-decimeter length ion source;
4) producing a ion accelerator;
5) producing an ion accelerator not limited by electric breakdown of walls due to electrostatic accelerating fields;
6) producing phase space volume occupied by the (and emittance of the) accelerated ions can be (arbitrarily) controlled by the density of the rarefied plasma and the external magnetic field strength;
7) producing a compact and (relatively) cheap laser system is used as a driver; and
8) producing an ion pickup not based on electrostatic acceleration.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for providing treatment, comprising:
    a chirped-pulse amplification (CPA) based, compact, high-repetition, high fluence laser system that produces an energy pulse,
    a light source guide system operatively connected to said laser system for guiding said energy pulse,
    a target system for receiving said energy pulse and producing an ion beam,
    an ion beam transport system transporting said ion beam, and
    a treatment field that receives said ion beam, wherein said ion beam transport system transports said ion beam to said treatment field.

2. The apparatus of claim 1 wherein said chirped-pulse amplification (CPA) based, compact, high-repetition, high fluence laser system is a Ti: sapphire laser chirped-pulse amplification (CPA) based, compact, high-repetition, high fluence laser system.

3. The apparatus of claim 1 wherein said chirped-pulse amplification (CPA) based, compact, high-repetition, high fluence laser system includes a pulse shaper that emits an energy pulse having a pulse energy of approximately 1 to approximately 10 Joules.

4. The apparatus of claim 1 wherein said chirped-pulse amplification (CPA) based, compact, high-repetition, high fluence laser system delivers pulses at a rate of approximately 0.1 to approximately 100 Hertz (Hz).

5. The apparatus of claim 1 wherein said chirped-pulse amplification (CPA) based, compact; high-repetition, high fluence laser system includes a pulse shaper.

6. The apparatus of claim 1 wherein said chirped-pulse amplification (CPA) based, compact, high-repetition, high fluence laser system includes a pulse shaper with a frequency multiplier.

7. The apparatus of claim 1 wherein said light source guide system includes a series of mirrors and thin foils.

8. The source apparatus of claim 1 wherein said energy pulse includes a prepulse and said light source guide system includes a series of thin foils capable of controlling or reducing said prepulse.

9. The apparatus of claim 1 wherein said energy pulse includes a prepulse and said light source guide system includes a series of thin metal foils capable of controlling or reducing said prepulse.

10. The apparatus of claim 1 wherein said laser system emits an energy pulse compressed into an ultrashort time scale of approximately 10 to 100 fs.

11. The apparatus of claim 1 wherein said laser system emits a light beam intensity in the range of approximately 1018 to 1023 Watts (W)/centimeter (cm)2.

12. The apparatus of claim 1 wherein said target system includes a foil.

13. The apparatus of claim 12 wherein said chirped-pulse amplification (CPA) based, compact, high-repetition, high fluence laser means delivers pulses at a rate of approximately 0.1 to approximately 100 Hertz (Hz).

14. The apparatus of claim 1 wherein said target system includes a prefoil.

15. The apparatus of claim 1 wherein said target system includes a film.

16. The apparatus of claim 1 wherein said target system includes a source and accelerator element.

17. The apparatus of claim 1 wherein said treatment field is a radiation oncology treatment field, or ion radiology treatment field, or spectroscopic diagnosis treatment field.

18. An apparatus for providing treatment, comprising:
    chirped-pulse amplification (CPA) based, compact, high-repetition, high fluence laser means for producing an energy pulse;
    a target means;
    a treatment field means,
    light source guide means for guiding said energy pulse to said target means, said light source guide means operatively connected to said laser means; and
    an ion beam transport means for transporting said ion beam to said treatment field means.

19. The apparatus of claim 18 wherein said chirped-pulse amplification (CPA) based, compact, high-repetition, high fluence laser means is a Ti: sapphire laser chirped-pulse amplification (CPA) based, compact, high-repetition, high fluence laser system.

20. The apparatus of claim 18 wherein said chirped-pulse amplification (CPA) based, compact, high-repetition, high fluence laser means includes a pulse shaper that emits an energy pulse having a pulse energy of approximately 1 to approximately 10 Joules.

21. The apparatus of claim 18 wherein said chirped-pulse amplification (CPA) based, compact, high-repetition, high fluence laser means includes a pulse shaper.

22. The apparatus of claim 18 wherein said chirped-pulse amplification (CPA) based, compact, high-repetition, high fluence laser means includes a pulse shaper with a frequency multiplier.

23. The apparatus of claim 18 wherein said light source guide means includes a series of mirrors and thin foils.

24. The apparatus of claim 18 wherein said means for producing an energy pulse includes a prepulse and said light source guide means includes a series of thin foils capable of controlling or reducing said prepulse.

25. The apparatus of claim 18 wherein said energy pulse includes a prepulse and said light source guide means includes a series of thin metal foils capable of controlling or reducing said prepulse.

26. The apparatus of claim 18 wherein said light source means emits an energy pulse compressed into an ultrashort time scale of approximately 10 to 100 fs.

27. The apparatus of claim 18 wherein said light source means emits a light beam intensity in the range of approximately 1018 to 1023 Watts (W)/centimeter (cm)2.

28. A method of providing treatment, comprising the steps of:
producing high power, short laser pulses utilizing a chirped-pulse amplification (CPA) based, compact, high-repetition, high fluence laser system;
guiding said energy pulses to a target for producing an ion beam; and
transporting said ion beam to a destination for treatment, wherein said step of transporting said beam to a destination for treatment comprises providing a treatment field and transporting said beam to said treatment field for treatment.

29. The method of providing treatment of claim 28 wherein said step of producing high power, short laser pulses utilizing a chirped-pulse amplification (CPA) based, compact, high-repetition, high fluence laser system utilizes a Ti: sapphire laser chirped-pulse amplification (CPA) based, compact, high-repetition, high fluence laser system.

30. The method of providing treatment of claim 28 wherein said step of producing high power, short laser pulses utilizing a chirped-pulse amplification (CPA) based, compact, high-repetition, high fluence laser system utilizes a pulse shaper that emits an energy pulse having a pulse energy of approximately 1 to approximately 10 Joules.

31. The method of providing treatment of claim 28 wherein said step of producing high power, short laser pulses utilizing a chirped-pulse amplification (CPA) based, compact, high-repetition, high fluence laser system delivers said pulses at a rate of approximately 0.1 to approximately 100 Hertz (Hz).

32. The method of providing treatment of claim 28 wherein said step of producing high power, short laser pulses utilizing a chirped-pulse amplification (CPA) based, compact, high-repetition, high fluence laser system utilizes energy pulses compressed into an ultrashort time scale of approximately 10 to 100 fs.

33. The method of providing treatment of claim 28 wherein said step of producing high power, short laser pulses utilizing a chirped-pulse amplification (CPA) based, compact, high-repetition, high fluence laser system utilizes a light beam intensity in the range of approximately 1018 to 1023 Watts (W)/centimeter (cm)2.

34. The method of providing treatment of claim 28 wherein said step of producing high power, short laser pulses utilizing a chirped-pulse amplification (CPA) based, compact, high-repetition, high fluence laser system produces an energy per laser shot of between approximately 1 and approximately 10 Joules.

35. The method of providing treatment of claim 28 wherein said step of guiding said energy pulses to a target produces a thin layer of overdense plasma.

36. The method of providing treatment of claim 35 wherein said thin layer of overdense plasma is carried through said overdense plasma layer and produces a magnetically underdense plasma and converts said magnetically underdense plasma into a coherent ion wave.

37. The method of providing treatment of claim 28 wherein said step of transporting said ion beam to a destination for treatment comprises transporting said ion beam to a destination for radiation oncology treatment, or ion radiology treatment, or spectroscopic diagnosis treatment.

* * * * *